United States Patent [19]

Honeyager

[11] Patent Number: 5,005,581

[45] Date of Patent: Apr. 9, 1991

[54] MOTION ARTIFACT DETECTION FOR CONTINUOUS BLOOD PRESSURE MONITOR TRANSDUCER

[75] Inventor: Kevin S. Honeyager, San Antonio, Tex.

[73] Assignee: Colin Electronics Co., Ltd., Aichi, Japan

[21] Appl. No.: 160,790

[22] Filed: Feb. 25, 1988

[51] Int. Cl.$^5$ .................................................. A61B 5/02
[52] U.S. Cl. ...................................... 128/681; 128/672
[58] Field of Search ............... 128/681, 682, 683, 672, 128/675

[56] References Cited

U.S. PATENT DOCUMENTS 4,349,034 9/1982 Ramsey, III .................... 128/682
4,423,738 1/1984 Newgard ........................ 128/672
4,543,962 10/1985 Medero et al. ................. 128/682

Primary Examiner—Lee S. Cohen
Assistant Examiner—Scott Getzow
Attorney, Agent, or Firm—Oliff & Berridge

[57] ABSTRACT

A method and apparatus is provided for detecting motion artifacts in data obtained from a blood pressure monitoring transducer and for preventing erroneous data related to such artifacts from interfering with the accuracy of the blood pressure measurement. Operation includes the steps of monitoring the amplitude of a pulse waveform from a first pulse to a next successive pulse and determining if the output signal changes by more than a predetermined percentage, thus indicating a motion condition.

3 Claims, 5 Drawing Sheets

MOTION ARTIFACT DETECTION FOR CONTINUOUS BLOOD PRESSURE MONITOR TRANSDUCER

FIELD OF THE INVENTION

The present invention relates generally to a method and apparatus for continuous noninvasive measurement of blood pressure. More specifically, the present invention provides a means for detecting motion artifacts and for preventing erroneous data related to said artifacts from interfering with the accuracy of the blood pressure measurement.

BACKGROUND

There has been considerable interest in recent years in the development of a monitoring system for obtaining a continuous measurement of a patient's blood pressure. One of the most promising techniques for obtaining such a continuous measurement involves the use of an arterial tonometer comprising an array of small pressure sensing elements fabricated in a silicon "chip". The use of such an array of sensor elements for blood pressure measurements is disclosed generally in the following U.S. Patents: U.S. Pat. No. 3,123,068 to R. P. Bigliano, U.S. Pat. No. 3,219,035 to G. L. Pressman, P. M. Newgard and John J. Eige, U.S. Pat. No. 3,880,145 to E. F. Blick, U.S. Pat. No. 4,269,193 to Eckerle, and U.S. Pat. No. 4,423,738 to P. M. Newgard, and in an article by G. L. Pressman and P. M. Newgard entitled "A Transducer for the Continuous External Measurement of Arterial Blood Pressure" (IEEE Trans. Bio-Med. Elec., Apr. 1963, pp. 73–81).

In a typical tonometric technique for monitoring blood pressure, a transducer which includes an array of pressure sensitive elements is positioned over a superficial artery, and a hold-down force is applied to the transducer so as to flatten the wall of the underlying artery without occluding the artery. The pressure sensitive elements in the array have at least one dimension smaller than the lumen of the underlying artery in which blood pressure is measured, and the transducer is positioned such that more than one of the individual pressure-sensitive elements is over at least a portion of the underlying artery. The output from one of the pressure sensitive elements is selected for monitoring blood pressure. The element that is substantially centered over the artery has a signal output that provides an accurate measure of intraarterial blood pressure. However, for the other transducer elements, the signal outputs generally do not provide as accurate a measure of intraarterial blood pressure as the output from the centered element. Generally, the offset upon which systolic and diastolic pressures depend will not be measured accurately using transducer elements that are not centered over the artery. In some prior art arrangements the pressure sensitive element having the maximum pulse amplitude output is selected, and in other arrangements the element having a local minimum of diastolic or systolic pressure which element is within substantially one artery diameter of the element which generates the waveform of maximum pulse amplitude is selected.

One of the difficulties encountered in the use of tonometric techniques for monitoring blood pressure is the sensitivity of the pressure sensing elements which makes them extremely susceptible to erroneous detection of motion artifacts as pressure waveforms. Such erroneous detection of motion can cause significant errors in the measured blood pressure. The method of the present invention, described in greater detail below, provides a means for detection of motion artifacts and for preventing pressure waveforms related to motion from erroneously being reported as blood pressure waveforms.

SUMMARY OF THE INVENTION

The present invention relates to a blood pressure monitoring system employing a transducer which comprises an array of individual pressure sensitive elements, each of which elements have at least one dimension smaller than the lumen of the underlying artery in which blood pressure is measured. The elements are of sufficiently small size such that with the array positioned so as to extend across the artery a plurality of elements are located over the artery. The outputs of all of the transducer elements are employed in locating the particular element which is centrally located over the artery. The output signal from this element, sometimes referred to as the "active element" is used to provide the measurement of blood pressure in the underlying artery.

In the method of the present invention, the amplitude of the pulse waveform reported by the active element is monitored from a first pulse to a next successive pulse to determine if the output signal changes by more than a predetermined percentage. If the predetermined threshold is exceed, the event is flagged as motion and data collection is temporarily halted. During successive pulses, the pulse pressure outputs of all of the pressure sensing elements are monitored and processed to determine the time at which the motion event ends. Data collection is resumed after the pulse waveforms for a predetermined number of successive pulses have been found to satisfy criteria indicating the absence of motion.

DETAILED DESCRIPTION OF THE PREFERRED EMBODIMENT

Figure 1:
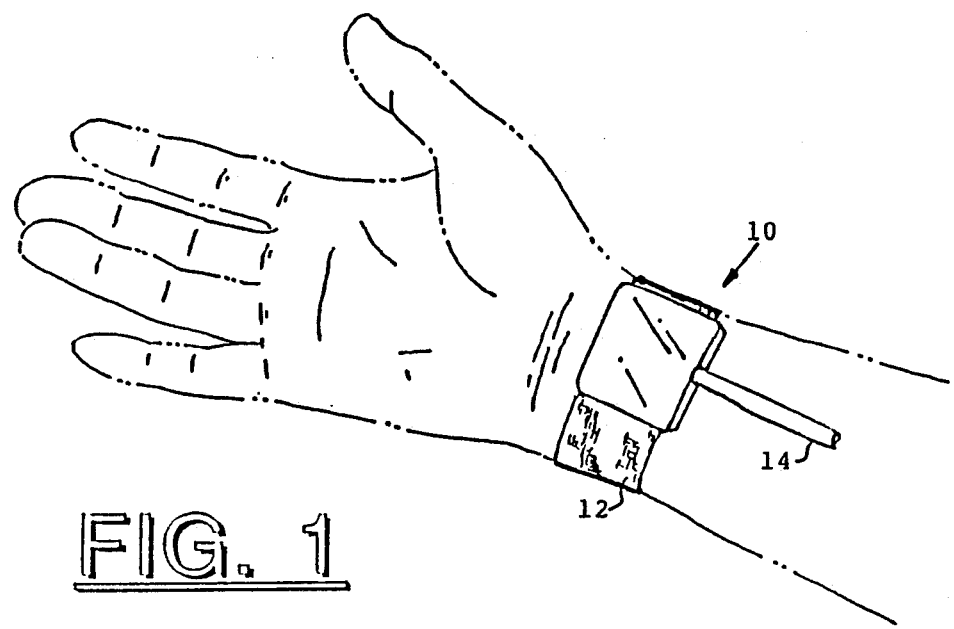
FIG. 1 is a view of the continuous blood pressure monitoring transducer of the present invention attached to a patient's wrist at a position overlying the radial artery.

Reference is now made to FIG. 1 wherein a continuous blood pressure monitor transducer 10 is shown attached to a patient's wrist at a point overlying the radial artery. The transducer is attached by means of a strap 12 in a manner similar to a conventional wristwatch. A cable assembly 14 connected to the transducer contains electrical cables for carrying electrical signals to and from the transducer. The cable assembly 12 also contains a pneumatic tube for providing pressurized air to a pressurizable bladder in the interior of the transducer in order to bring a sensor into contact with the patient's skin in a manner described in greater detail hereinbelow.

For the transducer to properly measure blood pressure it is important that the underlying artery be partially compressed. Specifically, it is important that the artery be flattened by a plane surface so that the stresses developed in the arterial wall perpendicular to the face of the sensor are negligible. This generally requires that the blood pressure measurement be taken on a superficial artery which runs over bone, against which the artery can be flattened.

Figure 2:
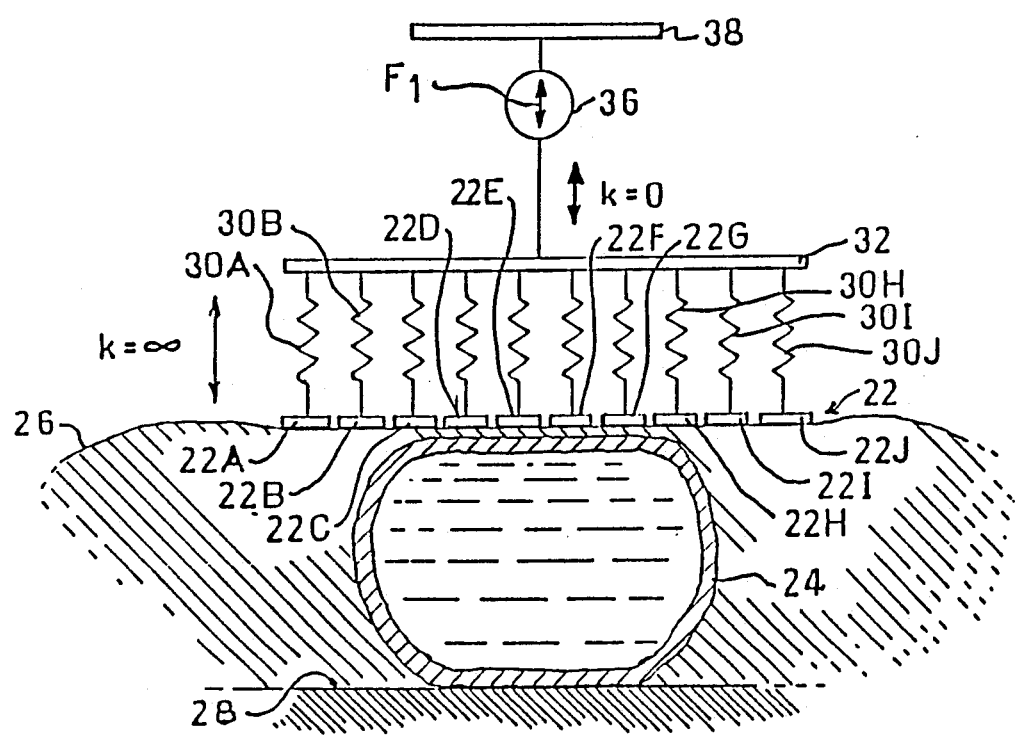
FIG. 2 is a schematic diagram illustrating the force balance between the artery and the multiple transducer elements (arterial riders), with the artery wall properly depressed to give accurate blood pressure readings.

Reference now is made to FIG. 2 wherein a diagrammatic mechanical model is shown which is representative of physical factors to be considered in blood pressure measurements using tonometry techniques. The illustrated model is adapted from that shown in the above-mentioned U.S. Pat. No. 4,269,193, issued to J. S. Eckerle, which by this reference is incorporated for all purposes. An array 22 of individual pressure sensitive elements or transducers 22-A through 22-E, which constitute the arterial riders, is positioned so that one or more of the riders are entirely over an artery 24. The individual riders 22-A through 22-E are small relative to the diameter of the artery 24, thus assuring that a plurality of the riders overlie the artery. The skin surface 26 and artery underlying the transducer must be flattened by application of a hold-down pressure to the transducer. One rider overlying the center of the artery is identified as the "centered" rider, from which rider pressure readings for monitoring blood pressure are obtained. Means for selecting the centered rider are discussed generally in the above mentioned U.S. Pat. No. 4,269,193. An improved method for locating the rider which best represents the actual waveform in the underlying artery is described in greater detail below. For present purposes it will be understood that one of the riders, such as rider 22-E, may be selected as the "centered" rider, in which case the remainder of the riders, here riders 22-A through 22-D and 22-F through 22-J, comprise "side plates" which serve to flatten the underlying skin and artery.

Superficial arteries, such as the radial artery, are supported from below by bone which, in FIG. 2, is illustrated by ground symbol 28 under the artery. The wall of artery 24 behaves substantially like a membrane in that it transmits tension forces but not bending moments. The artery wall responds to the loading force of the transducer array, and during blood pressure measurements acts as if it is resting on the firm base 28. With the illustrated system, the transducer assembly 10 and mounting strap 12, together with air pressure applied to a pressurizable bladder in the transducer assembly, supply the required compression force and hold the riders 22-A through 22-J in such a manner that arterial pressure changes are transferred to the riders which overlie the artery 24. This is illustrated schematically in FIG. 2 by showing the individual riders 22-A through 22-J backed by rider spring members 30-A through 30-J, respectively, a rigid spring backing plate 32, and hold-down force generator 36 between the backing plate 32 and the mounting strap system 38.

If, without force generator 36, the coupling between the mounting strap system 38 and spring backing plate 32 were infinitely stiff to restrain the riders 22-A through 22-J rigidly with respect to the bone structure 28, the riders would be maintained in a fixed position relative to the artery. In practice, however, such a system is not practical, and hold-down force generator 36, comprising (in the present example) a pneumatic loading system, is included to keep constant the force applied by the mounting strap system 38 to riders 22-A through 22-J. In the mechanical model the spring constant, k (force per unit of deflection) of the force generator, 36, is nearly zero. Pneumatic loading systems are shown and described in the above-referenced U.S. Pat. Nos. 3,219,035 and 4,269,193, and the Pressman and Newgard IEEE article. In addition, an improved pneumatic loading system is disclosed in a patent application entitled "Pressurization System for Continuous Blood Pressure Monitor Transducer" filed on even data herewith.

In order to insure that the riders 22-A through 22-J flatten the artery and provide a true blood pressure measurement, they must be rigidly mounted to the backing plate 32. Hence, the rider springs 30-A through 30-J of the device ideally are infinitely rigid (spring constant $k = \infty$). It is found that as long as the system operates in such a manner that it can be simulated by rider springs 30-A through 30-J having a spring constant on the order of about ten times the corresponding constant for the artery-skin system, so that the deflection of riders 22-A through 22-J is small, a true blood pressure measurement may be obtained when the correct hold-down pressure is employed.

Figure 3:
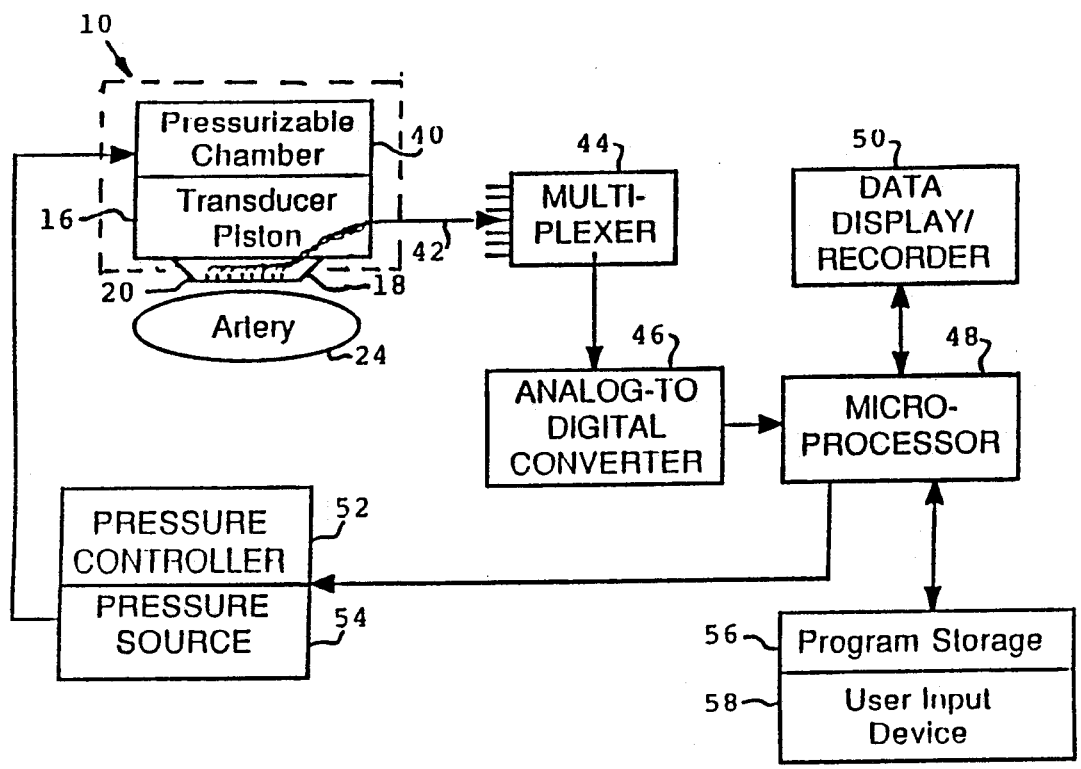
FIG. 3 is a simplified block diagram of the transducer assembly and associated system components for the continuous blood pressure monitoring system of the present invention.

Referring to FIG. 3, a simplified illustration of the transducer assembly 10 is shown to include a transducer piston 16, a pressurizable chamber 40. The output of the individual pressure sensors (not shown) on the sensor 20 are connected by appropriate electrical wiring 42 to the input of a multiplexer 44. From the multiplexer, the signals are digitized by an analog-to-digital (A-D) converter 46, and the digitized signals are supplied to a microprocessor 48. Output from the microprocessor 48 is supplied to data display and recorder means 50 which may include a recorder, cathode ray tube monitor, a solid state display, or any other suitable display device. Also, the output from the microprocessor is provided to the pressure controller 53 which controls a pressure source 54 to maintain the appropriate hold down pressure for the transducer piston 16. Operation of the microprocessor can be controlled by a program contained in program storage 56 or by user input from the user input device, which can be in the form of a keyboard or other interface device.

Figure 4:
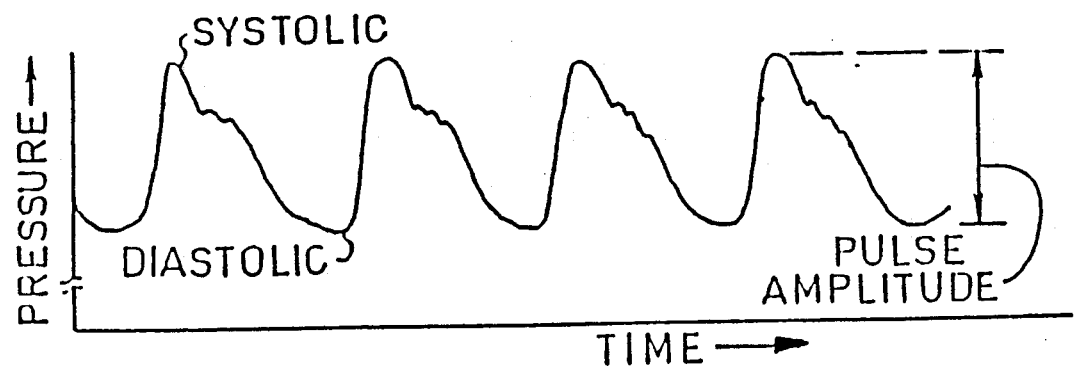
FIG. 4 is a waveform of human blood pressure versus time of the type which may be obtained using the present invention for illustrating systolic and diastolic pressures and pulse amplitude of the blood pressure wave.

Reference is now made to FIG. 4 which illustrates the signal waveform of the output from one of the pressure sensitive elements 22-A through 22-J which overlies artery 24. Other elements of the transducer array which overlie the artery will have waveforms of similar shape. With a correct hold-down pressure and correct selection of the "centered" arterial rider (i.e., the rider substantially centered over the artery) the waveform is representative of the blood pressure within the underlying artery. Systolic, diastolic and pulse amplitude pressures are indicated on the waveform, wherein pulse amplitude is the difference between the systolic and diastolic pressures for a given heartbeat.

Figure 5A:
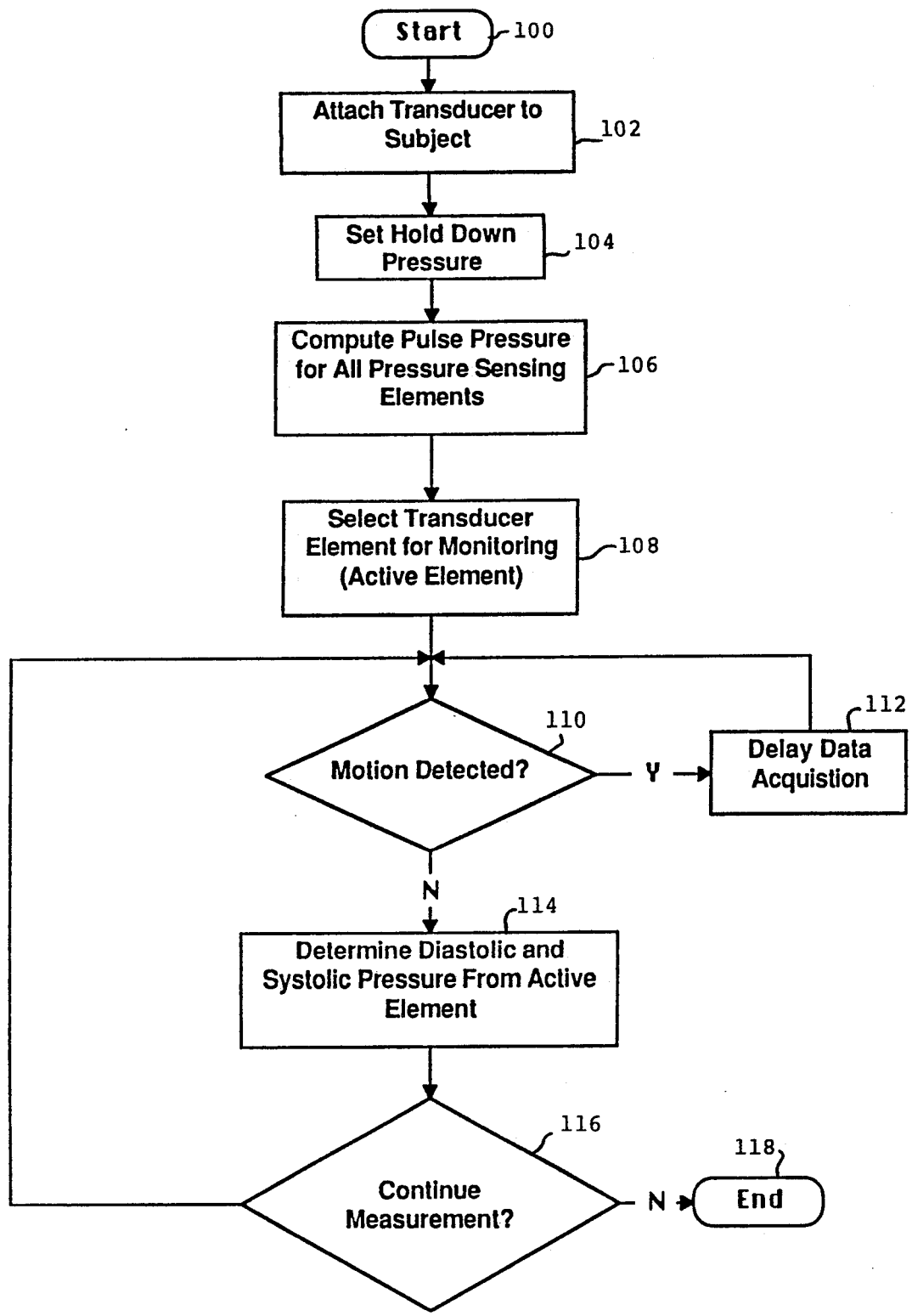
FIGS. 5A–5C together show a flow chart for use in explaining overall operation of this invention.
Figure 5B:
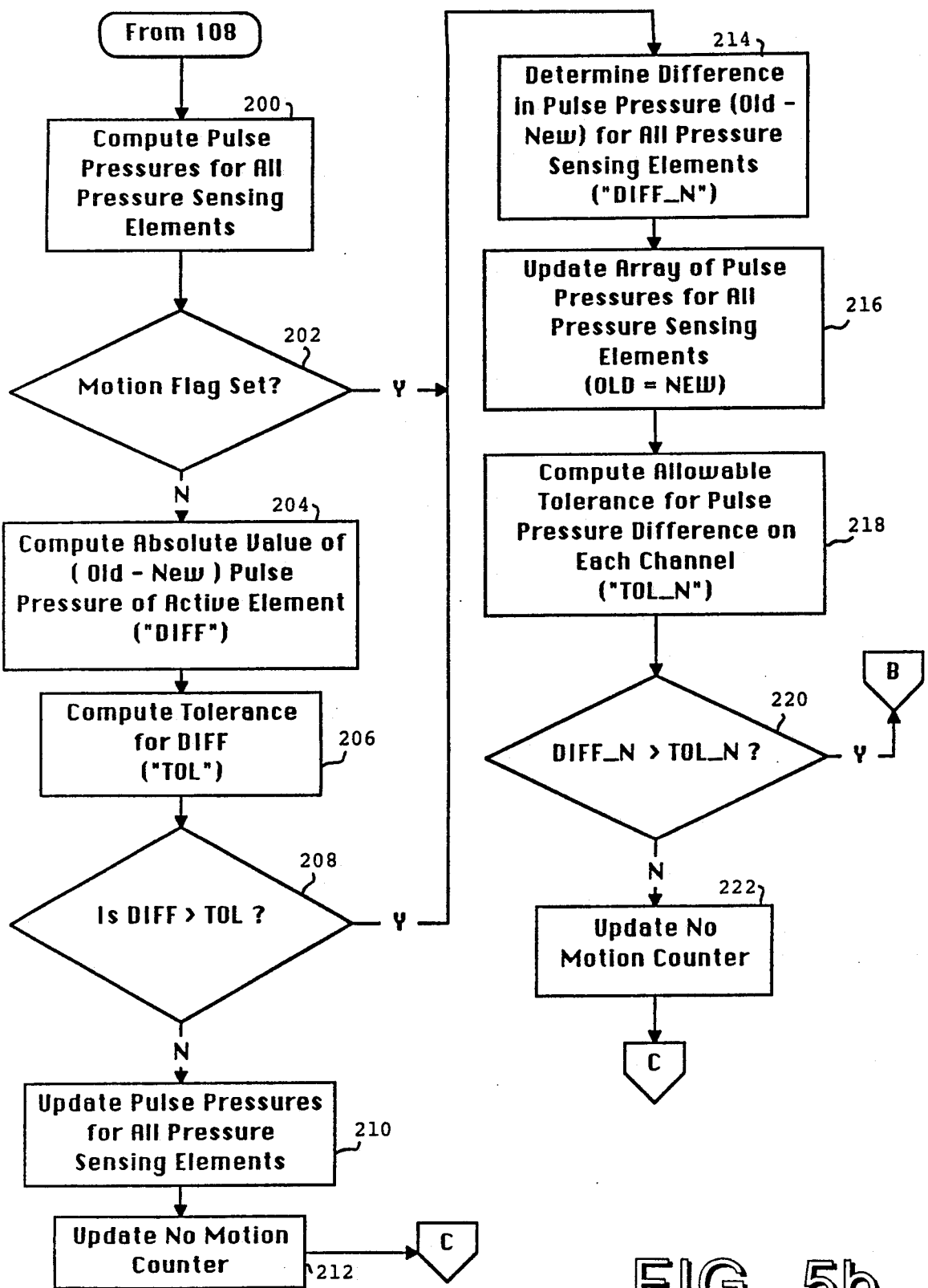
Figure 5C:
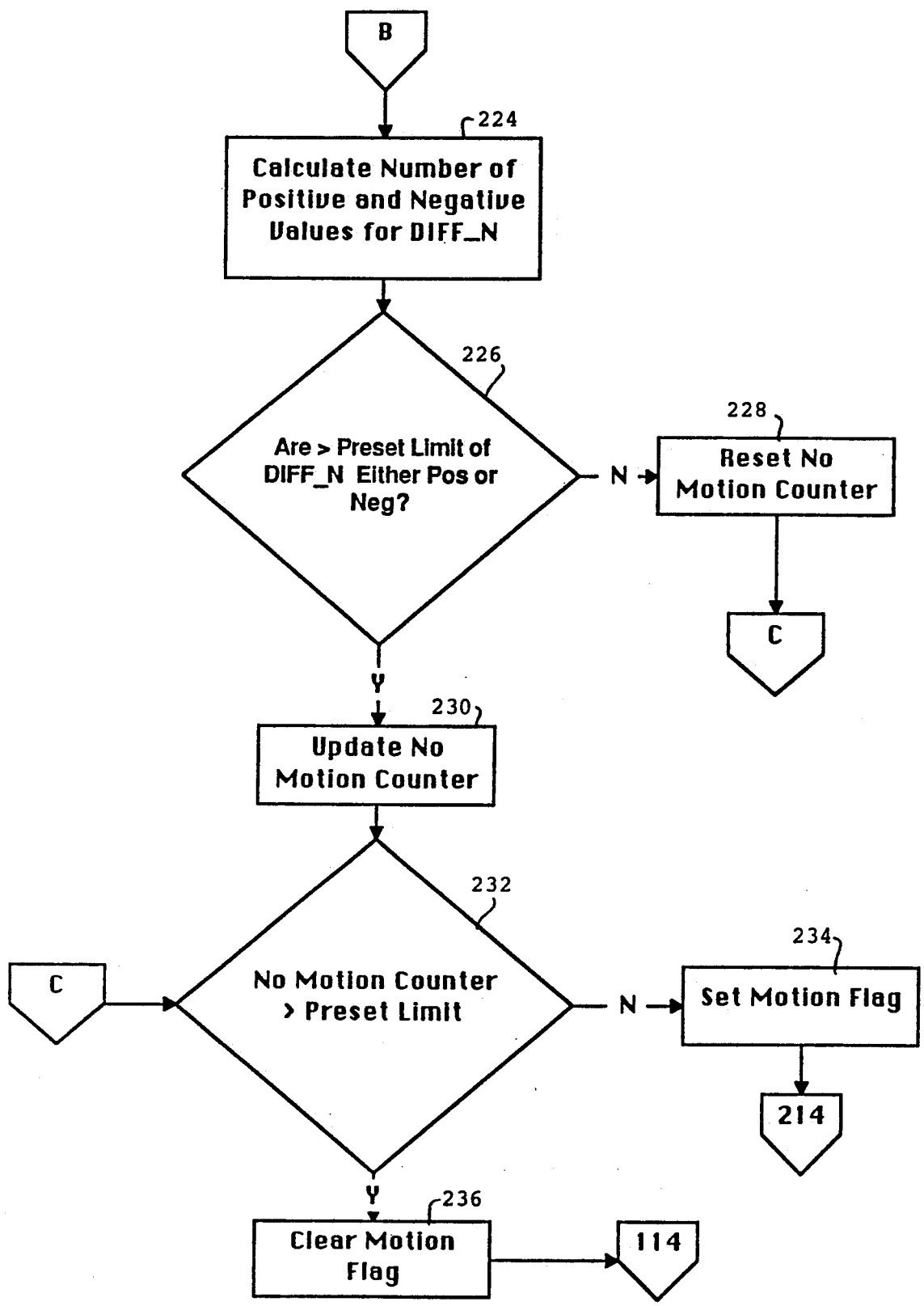

FIGS. 5a–5c together show a flow chart of an algorithm for general overall operation of the blood pressure monitoring system. Some of the operations indicated therein are under control of the microprocessor 48 responsive to programming instructions contained in program storage 56. Obviously, several program steps may be involved in the actual implementation of the indicated operations. Since the programming of such steps is well within the skill of the average programmer, a complete program listing is not required and is not included herein.

Preparation for monitoring is begun at START, step 100, at which time system power is turned on or a reset operation is performed by means not shown, and counters, registers, and timers in microprocessor 48 are initialized. The transducer is attached to the subject at step 102 at a location wherein at least one transducer element, such as element 22-E of Transducer Array 22 should overly the center of the artery 24. Next, at step 104, a hold down pressure is applied wherein air under pressure from source 54 is applied to the transducer. With the transducer attached to the subject, step 106 is entered wherein the pulse pressure for all pressure sensing elements is computed. In step 108, a transducer element is selected for monitoring pulse pressure in the underlying artery. At step 110, a decision is made about whether motion has been detected. If the answer to this question is affirmative, then the acquisition of data is delayed as indicated in step 112. Details relating to the steps implemented in motion detection and delay of data acquisition will be discussed below in the flow charts of FIGS. 5b and 5c. If no motion is detected, step 114 is entered wherein diastolic and systolic pressure are computed from the output signal produced by the active element. In step 116, a determination is made of whether to continue taking measurements of blood pressure. If the answer to this question is negative, then the processing ends in step 118. If the answer is affirmative, then step 110 is re-entered and the blood pressure measurement cycle continues.

Details relating to the processing steps for implementing steps 110 and 112 are shown in FIGS. 5B and 5C. Beginning at step 200 in FIG. 5B, the pulse pressures are computed for all pressure sensing elements. In step 202, a determination is made regarding the existence of a motion flag. If no motion flag is previously set, then step 204 is entered; otherwise step 214, discussed below, is entered. In step 204, the absolute value of the new values for pulse pressure minus the old values for pulse pressure are computed for the active element, with the resulting value being represented by the variable "DIFF". In step 206, a tolerance is computed for an acceptable difference, which is indicated by the variable "TOL". In the preferred embodiment, the tolerance is set at 25%. In step 208, a decision is made to determine whether the value of DIFF is greater than TOL. If the answer to this determination is negative, then step 210 is entered wherein pulse pressures for all pressure sensing elements are updated. Then, in step 212 the no motion counter is updated. If the answer to the determination in step 208 is affirmative, then step 214 is entered wherein the difference is calculated between all old values of pulse pressures and all new values of pulse pressures for the pressure sensing elements. These differences are identified by the variable "DIFF_N". In step 216, the array of pulse pressures for all pressure sensing elements is updated, with the old values being replaced by the new values computed in step 214. In step 218, an allowable tolerance is computed for the pulse pressure difference on each channel of the pressure sensing elements, with this tolerance being identified by the variable "TOL_N". In the preferred embodiment, this tolerance is again at 25%. In step 220, a decision is made regarding whether DIFF_N is greater than TOL_N. If the answer to this determination is negative, step 222 is entered wherein the no motion counter is updated. If the answer to this determination is affirmative, then step 224 is entered, wherein the values for DIFF_N are classified as being either positive or negative. In step 226, a determination is made regarding whether more than a preset limit of DIFF_N are either positive or negative. In the preferred embodiment, 13 out of 15 of the pressure sensing elements must have either a positive or a negative change for the no motion counter to be updates. This ratio is chosen because actual changes in blood pressure tend to be indicated on a large fraction of the pressure sensing elements, while motion-related pressure changes tend not to be so uniformly reflected in all of the pressure sensing elements. If the answer to this determination is negative, then step 228 is entered, wherein the no motion counter is reset. However, if the answer to the determination of step 226 is affirmative, then step 230 is entered, wherein the no motion counter is updated. In step 232, a determination is made regarding whether the no motion counter exceeds a preset limit. In the preferred embodiment, the limit is set at four consecutive counts indicating lack of motion. If the determination of step 232 is affirmative, then the motion flag is cleared an the system returns to step 114 for the calculation of blood pressure. However, if the answer to the determination of step 232 is negative, then the motion flag is set and the system returns to step 214.

Although the method and apparatus of the present invention has been described in connection with the preferred embodiment, it is not intended to be limited to the specific form set forth herein, but on the contrary, it is intended to cover alternatives and equivalents as may reasonable be included within the spirit and scope of the invention as defined by the appended claims.

I claim:

1. A method for detecting motion artifacts in data obtained from a blood pressure monitoring transducer, comprising the steps of:

monitoring a plurality of pressure sensing elements overlying an artery, said pressure sensing elements each producing a pulse amplitude signal waveform indicative of the pressure in said artery during successive pulses;

calculating a predetermined percentage of the pulse amplitude signals produced by said pressure sensing elements during a first pulse;

measuring the pulse amplitude signals produced by said pressure sensing elements on a next successive pulse and comparing the respective pulse amplitudes produced by said pressure sensing elements with the pulse amplitudes produced by the respective pressure sensing element during said first pulse; and indicating a motion condition if any of said pulse amplitude signals measured during said next successive pulse differ from the corresponding pulse amplitude produced during said first pulse, by more than said predetermined percentage.

2. The method of claim 1, wherein the monitoring step includes collection of data and further including the step of:

interrupting the collection of data from said pressure sensing elements upon said indication of a motion condition.

3. An apparatus for detecting motion artifacts in data obtained from a blood pressure monitoring transducer, said apparatus comprising:

means for monitoring a plurality of pressure sensing elements overlying an artery, said pressure sensing elements each producing a pulse amplitude signal waveform indicative of the pressure in said artery during successive pulses;

means for calculating a predetermined percentage of the pulse amplitude signals produced by said pressure sensing elements during a first pulse;

means for measuring the pulse amplitude signals produced by said pressure sensing elements on a next successive pulse and comparing the respective pulse amplitudes produced by said pressure sensing elements with the pulse amplitudes produced by the respective pressure sensing element during said first pulse; and means for indicating a motion condition if any of said pulse amplitude signals measured during said next successive pulse differ from the corresponding pulse amplitude produced during said first pulse, by more than said predetermined percentage.

* * * * *